United States Patent
Helms et al.

(10) Patent No.: US 11,911,254 B1
(45) Date of Patent: Feb. 27, 2024

(54) MALE CONTINENCE DEVICE

(71) Applicants: Richard A. Helms, Big Lake, MN (US); Ken L. Adam, Chanhassen, MN (US); Lewis A. Ratajczak, Milaca, MN (US); Joseph T. Mahon, Minneapolis, MN (US); Scott A. Olson, Zimmerman, MN (US)

(72) Inventors: Richard A. Helms, Big Lake, MN (US); Ken L. Adam, Chanhassen, MN (US); Lewis A. Ratajczak, Milaca, MN (US); Joseph T. Mahon, Minneapolis, MN (US); Scott A. Olson, Zimmerman, MN (US)

( * ) Notice: Subject to any disclaimer, the term of this patent is extended or adjusted under 35 U.S.C. 154(b) by 0 days.

(21) Appl. No.: 18/159,082

(22) Filed: Jan. 24, 2023

Related U.S. Application Data

(62) Division of application No. 17/842,769, filed on Jun. 16, 2022, now Pat. No. 11,583,380.

(51) Int. Cl.
*A61F 2/00* (2006.01)
*A61F 2/26* (2006.01)

(52) U.S. Cl.
CPC .............. *A61F 2/0036* (2013.01); *A61F 2/26* (2013.01)

(58) Field of Classification Search
CPC .... A61F 2/0036; A61F 2/0004; A61F 2/0031; A61F 2/0054; A61F 2/26
See application file for complete search history.

(56) References Cited

U.S. PATENT DOCUMENTS

| | | | | |
|---|---|---|---|---|
| 3,926,175 A | * | 12/1975 | Allen | A61F 2/0036 251/9 |
| 4,551,862 A | * | 11/1985 | Haber | A61F 2/0036 600/491 |
| 5,184,629 A | * | 2/1993 | Erickson | A61F 2/0054 128/885 |
| 7,223,228 B2 | * | 5/2007 | Timm | A61F 2/0036 600/30 |
| 2012/0053397 A1 | * | 3/2012 | Deegan | A61F 2/0036 600/30 |

\* cited by examiner

*Primary Examiner* — Christine H Matthews
(74) *Attorney, Agent, or Firm* — Albert W. Watkins

(57) ABSTRACT

A surgically implanted occluding assembly comprises an implant body having a longitudinally split generally "C"-shaped cross-section tube circumscribing an anatomical lumen. In one embodiment, the surgically implanted occluding assembly is a male continence device selectively occluding a urethra. In some embodiments an occluding magnet is rigidly affixed with the implant body, and an external selective occlusion control assembly is used to selectively activate the surgically implanted occluding assembly. The external assembly has a magnet, and body supporting the magnet. The external selective occlusion control assembly is configured to be selectively placed and retained adjacent to the surgically implanted occluding assembly. In some embodiments, a bi-stable spring longer than and spanning the longitudinal split in the implant body has a first stable anatomical lumen occluding position curved into an interior of the longitudinal split, and a second stable anatomical lumen open position curved outward exterior of the longitudinally split tube.

8 Claims, 5 Drawing Sheets

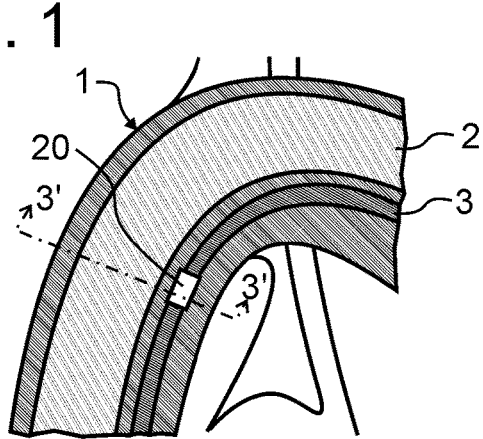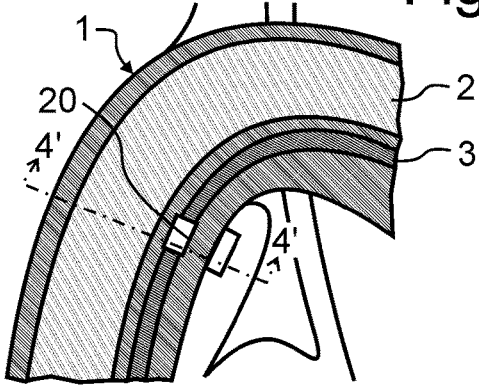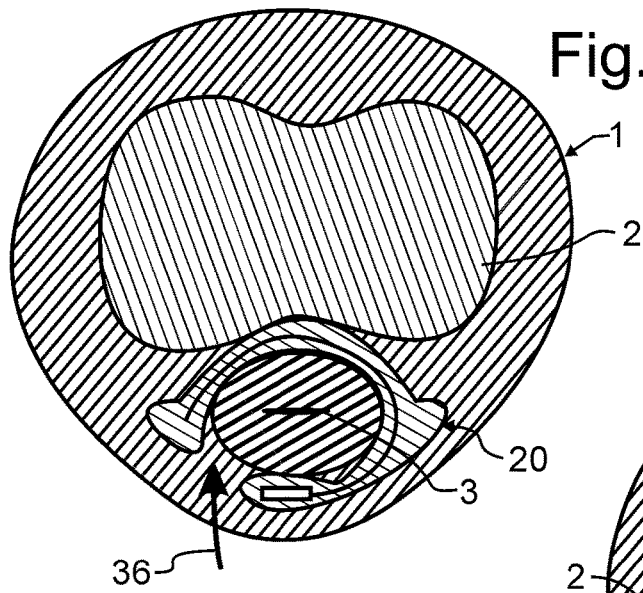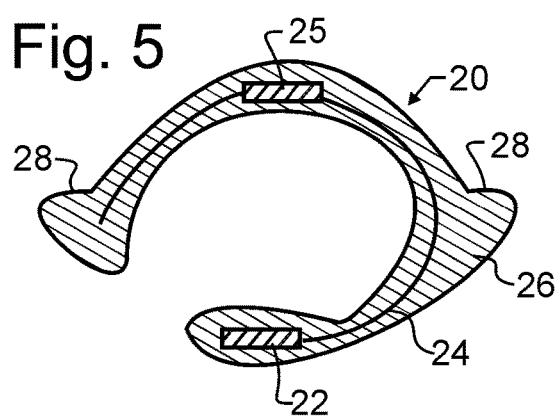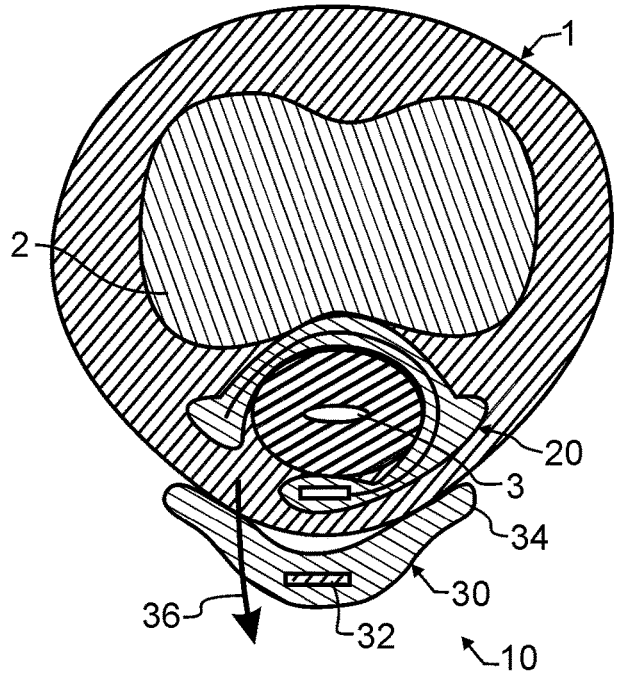

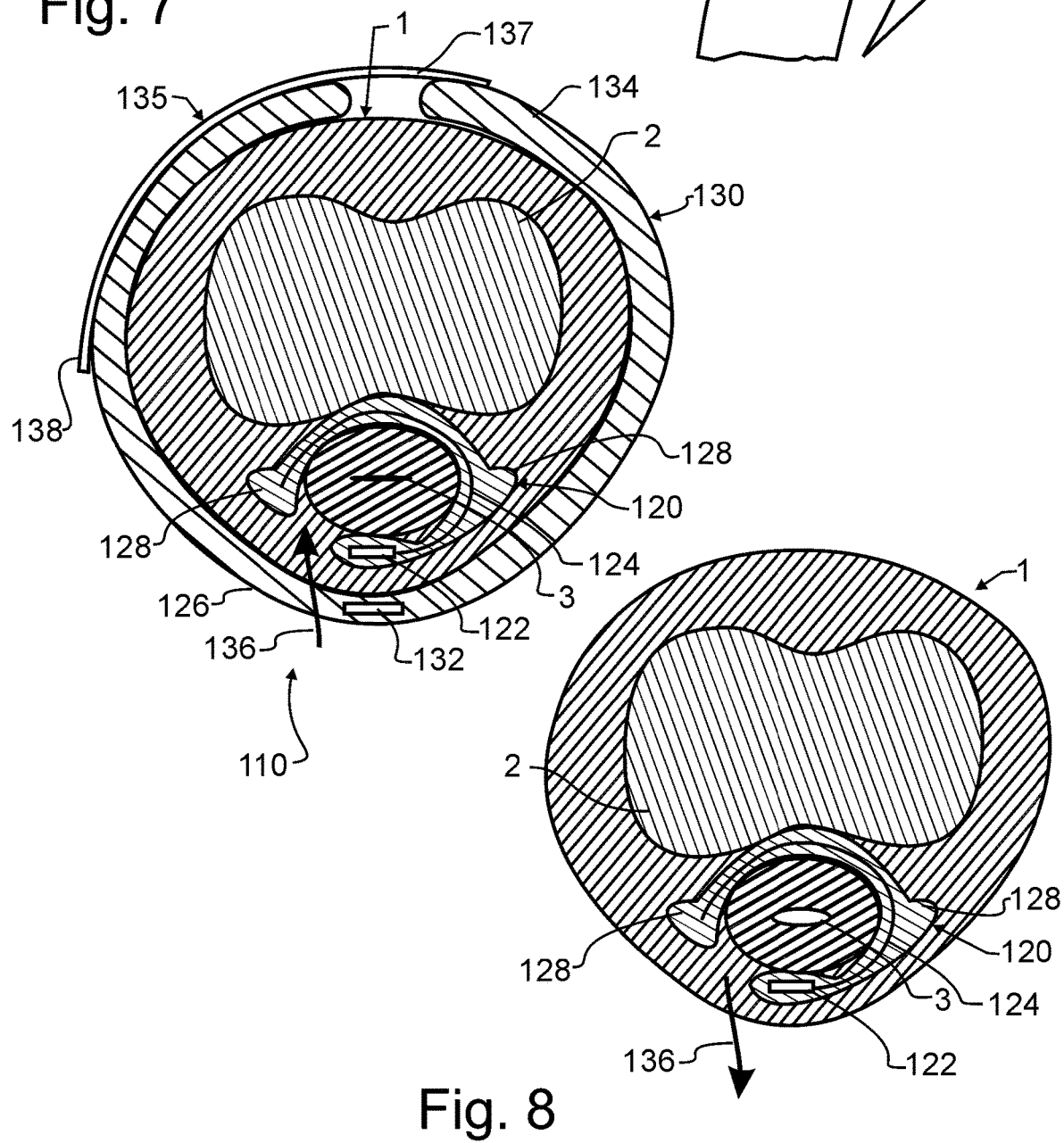

Fig. 9
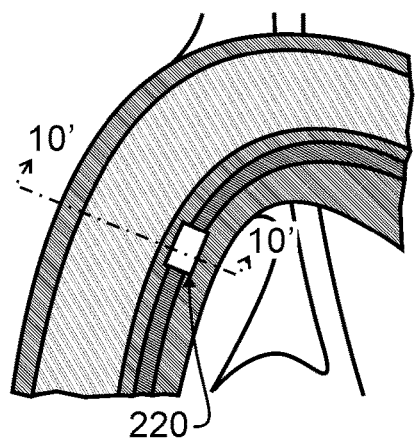
Fig. 10
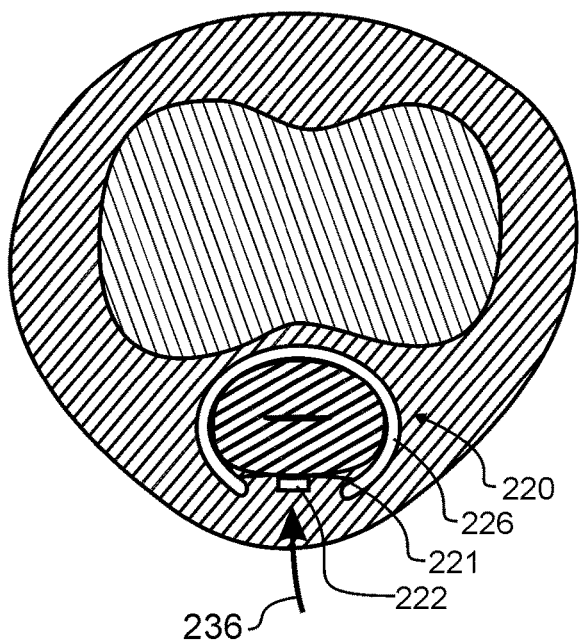
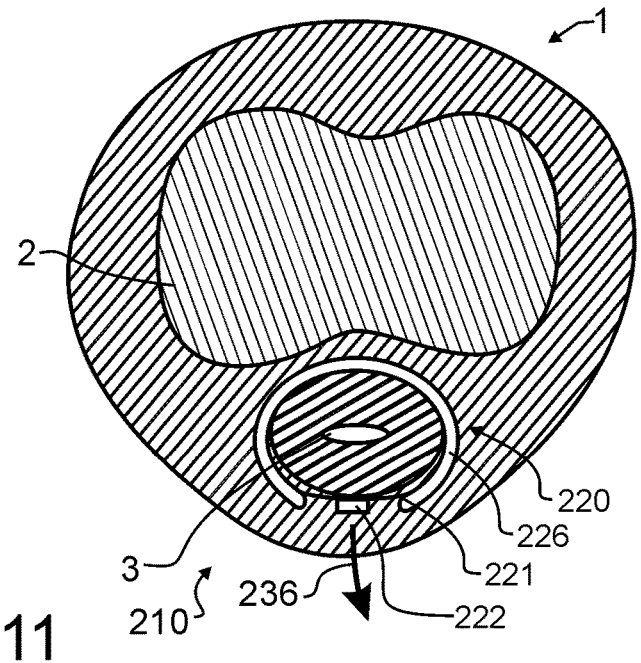
Fig. 11

MALE CONTINENCE DEVICE

BACKGROUND OF THE INVENTION

1. Field of the Invention

The invention pertains generally to a body-implanted lumen occluding apparatus. In a more particular manifestation, the invention pertains to an apparatus for controlling urinary incontinence.

2. Description of the Related Art

For various reasons, a large number of persons are affected by urinary incontinence. While more common with increasing age, many other factors can cause incontinence. With this incontinence can come a fear of accidents and associated urine odor. These can very deleteriously affect a person's ability to function in society. As a result, impacts of incontinence can all too often include the need to move an affected person into an assisted living or other care facility.

Laminates having exceptional absorbency and liquid holding properties have heretofore been developed and advanced substantially. Originally commercially primarily applied to diapers and feminine hygiene products, this technology has been extended to adult use explicitly to address incontinence. While a significant improvement, these adult diapers have a number of commercial and practical drawbacks. In particular, the diapers: are still associated with a urine odor, are associated with a greater incidence of skin maladies in a population often already troubled by skin ailments; can accidentally and unexpectedly leak; and can be very expensive to use over time and generate substantial landfill waste, a fact that is particularly vexing when only a small amount of urine is released in any day. The health, financial, functional, and environmental disincentives are further compounded by the stigma and embarrassment associated with the purchase and wearing these adult diapers.

Others have proposed various mechanical apparatus to selectively occlude the urethra. There are many such devices, including various clamps, compression bands, and urine collection bags. The clamps and compression bands can only be used for very limited time periods, owing to the very elevated risk of tissue damage and necrosis. Urine collection bags are difficult to put on, and are prone to surprise leaks.

One particularly popular apparatus comprises a selectively fluid-inflated sphincter. When the sphincter is fluid-inflated, the urethra is occluded. When deflated, the urethra remains open. While offering a number of benefits, this apparatus is large, difficult to implant, and subject to poorer reliability than desired.

Recognizing the limitations of the prior art, a number of experts in the industry have proposed various mechanical apparatus that use more reliable magnets to selectively occlude the urethra. Exemplary U.S. patents, the teachings which are incorporated herein by reference, include: 3,939,821 by Roth, entitled "Magnetically actuated tube compressing valve"; 5,184,629 by Erickson et al, entitled "Male urinary anti-incontinence device and method"; 5,997,467 by Connolly, entitled "Urinary incontinence device"; 6,171,231 by Connolly, entitled "Urinary incontinence device"; 6,540,665 by Connolly, entitled "Urinary incontinence device"; 7,223,228 by Timm et al, entitled "Urethral occlusive assembly for preventing urinary incontinence"; and 7,658,194 by Anderson et al, entitled "Penile compression device".

Additional U.S. patents of varying relevance, the relevant teachings and contents which are incorporated herein by reference, include: 4,024,855 by Bucalo, entitled "Magnetic filamentary structure and method for using the same"; 4,191,196 by Bradley et al, entitled "Profilometry method and apparatus"; 4,846,818 by Keldahl et al, entitled "Incontinence appliance"; 4,850,963 by Sparks et al, entitled "Apparatus and methods for achieving urinary continence"; 4,994,019 by Fernandez et al, entitled "Magnetic occluding device"; 5,509,888 by Miller, entitled "Controller valve device and method"; 5,562,598 by Whalen et al, entitled "Artificial urethral sphincter"; 5,704,893 by Timm, entitled "Vessel occlusive apparatus and method"; 6,074,341 by Anderson et al, entitled "Vessel occlusive apparatus and method"; 6,179,769 by Ishikawa et al, entitled "Magnetic stimulus type urinary incontinence treatment apparatus"; 6,409,656 by Sangouard et al, entitled "Artificial sphincter with magnetic control"; 7,926,489 by Anderson et al, entitled "Penile compression device"; 8,007,429 by Anderson et al, entitled "Vessel occlusive device and method of occluding a vessel"; 8,062,205 by Timm et al, entitled "Drug elution for implantable incontinence devices"; and 8,753,363 by Anderson et al, entitled "Vessel occlusive device and method of occluding a vessel".

As may be apparent, in spite of the enormous advancements and substantial research and development that has been conducted, there still remains a need for a more readily surgically implanted lumen-occluding apparatus that functions effectively for extended periods without erosion or necrosis of vital tissue.

In addition to the foregoing patents, Webster's New Universal Unabridged Dictionary, Second Edition copyright 1983, is incorporated herein by reference in entirety for the definitions of words and terms used herein.

SUMMARY OF THE INVENTION

In a first manifestation, the invention is a male continence device. A surgically implanted occluding assembly has an implant body having a longitudinally split tube of generally "C"-shaped cross-section. An occluding magnet is rigidly affixed with the implant body adjacent one end of the implant body. At least one means is further provided for coupling the elastomeric body to penile tissue. An external selective occlusion control assembly is used to selectively activate or deactivate the surgically implanted occluding assembly and thereby selectively occlude a urethra. The external selective occlusion control assembly has an external selective control magnet, and an external selective occlusion body supporting the external selective control magnet. The external selective occlusion control assembly is configured to be selectively placed and retained adjacent to the surgically implanted occluding assembly, and subsequently selectively removed therefrom.

In a second manifestation, the invention is a surgically implanted occluding assembly and an anatomical lumen. The surgically implanted occluding assembly comprises an implant body having a longitudinally split tube of generally "C"-shaped cross-section circumscribing the anatomical lumen; and a bi-stable spring longer than and spanning the longitudinal split in the implant body; and has a first stable anatomical lumen occluding position curved into an interior of the longitudinal split thereby configured to occlude the anatomical lumen, and a second stable anatomical lumen open position curved outward exterior of the longitudinally split tube and thereby configured to leave the anatomical lumen un-occluded.

OBJECTS OF THE INVENTION

Exemplary embodiments of the present invention solve inadequacies of the prior art by providing a surgically implanted occluding assembly and, in most embodiments, an external selective occlusion control assembly. Spring or magnetic properties are combined with or opposed by magnetic and in some embodiments manual force to trigger a change from a urethral occluding state to an open state.

The present invention and the preferred and alternative embodiments have been developed with a number of objectives in mind. While not all of these objectives are found in every embodiment, these objectives nevertheless provide a sense of the general intent and the many possible benefits that are available from embodiments of the present invention.

A first object of the invention is to provide an apparatus that both effectively and selectively occludes a lumen, in particular the urethra. A second object of the invention is to provide a surgically implanted lumen-occluding apparatus that functions effectively for extended periods without erosion or necrosis of vital tissue. Another object of the present invention is to provide a single assembly to surgically implant that is both intuitive and configured to readily align with tissue surrounding the urethra during surgical installation. A further object of the invention is to provide a reduced number of components within a single implanted assembly to thereby improve reliability and simplify fabrication. Yet another object of the present invention is to provide a male continence device of minimal size to reduce the likelihood of discomfort or harm. An additional object of the invention is to provide an intuitive-to-use, external, and removable apparatus that interacts with the surgically implanted lumen-occluding apparatus to selectively control the occlusion or lack thereof of the lumen. An even further object of the invention is to constrain and control a path the occluding magnet travels through to minimal torsional stress on the surrounding tissue even in the event of misalignment between an external selective control magnet and an occluding magnet.

BRIEF DESCRIPTION OF THE DRAWINGS

The foregoing and other objects, advantages, and novel features of the present invention can be understood and appreciated by reference to the following detailed description of the invention, taken in conjunction with the accompanying drawings, in which:

FIG. 1 illustrates a preferred embodiment occluding assembly designed in accord with the teachings of the present invention and surgically implanted into a male penis from a vertical plane section view.

FIG. 2 illustrates a preferred embodiment male continence device including the preferred embodiment occluding assembly of FIG. 1 and a preferred embodiment external selective occlusion control assembly from a vertical plane section view similar to that of FIG. 1.

FIG. 3 illustrates the preferred embodiment surgically implanted occluding assembly of FIG. 1 from a cross-sectional view taken along a plane transverse to the male penis as represented by section line 3' in FIG. 1, and showing the urethra occluded.

FIG. 4 illustrates the preferred embodiment male continence device of FIG. 2 from a cross-sectional view taken along a plane transverse to the male penis as represented by section line 4' in FIG. 2, and showing the urethra un-occluded.

FIG. 5 illustrates the preferred embodiment occluding assembly of FIG. 1 from a cross-sectional view similar to that of FIG. 3, but somewhat enlarged and prior to surgical implantation, and further including an optional magnetically susceptible or magnetic material.

FIG. 6 illustrates a first alternative embodiment male continence device from a side elevational view.

FIG. 7 illustrates the first alternative embodiment male continence device of FIG. 6 from a cross-sectional view taken along a plane transverse to the male penis as represented by section line 7' in FIG. 6 and showing the urethra occluded.

FIG. 8 illustrates the first alternative embodiment surgically implanted occluding assembly of FIG. 7 from a cross-sectional view taken along a plane transverse to the male penis as represented by section line 7' in FIG. 6, but without the external selective occlusion control assembly and showing the urethra un-occluded.

FIG. 9 illustrates a second alternative embodiment surgically implanted occluding assembly from a side elevational view, with an occluding magnet and without suture wings.

FIG. 10 illustrates the second alternative embodiment surgically implanted occluding assembly of FIG. 9 from a cross-sectional view taken along a plane transverse to the male penis as represented by section line 10' in FIG. 9 and showing the urethra occluded.

FIG. 11 illustrates the second alternative embodiment surgically implanted occluding assembly of FIG. 9 from a cross-sectional view taken along a plane transverse to the male penis as represented by section line 10' in FIG. 9 and showing the urethra un-occluded.

DESCRIPTION OF THE PREFERRED EMBODIMENT

Figure 12:
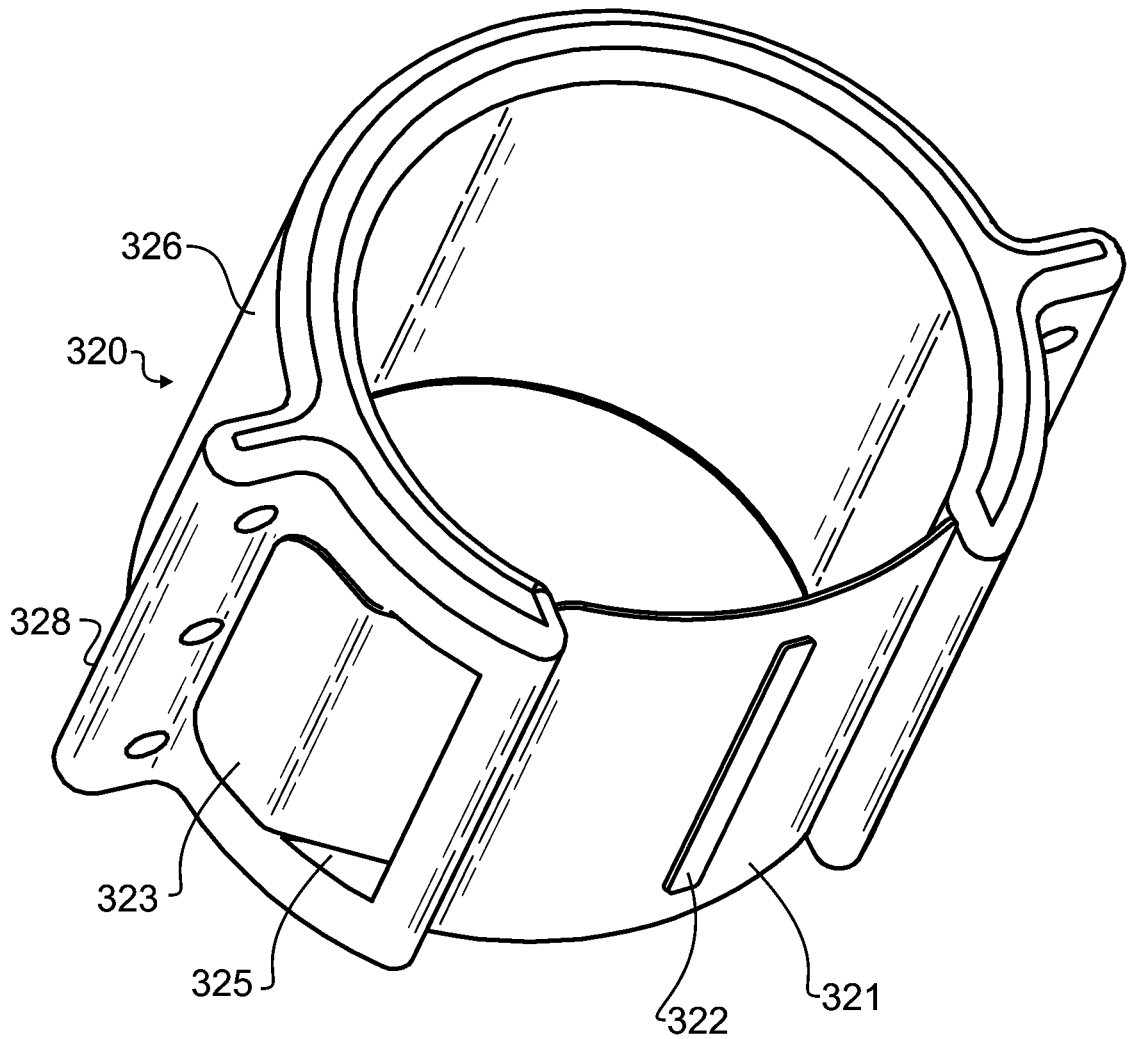
FIG. 12 illustrates the second alternative embodiment occluding assembly of FIG. 9 from a projected view, prior to surgical implanting and with an occluding magnet and with suture wings.

Manifested in the preferred embodiment, the present invention provides a male continence device 10 having a surgically implanted occluding assembly 20 and an external selective occlusion control assembly 30. As illustrated in FIGS. 1-4, occluding assembly 20 is illustrated surgically implanted into a male penis 1, with the corpora cavernosa 2 and urethra 3 specifically illustrated and identified.

Surgically implanted occluding assembly 20, which is illustrated prior to surgical implantation in FIG. 5, comprises an occluding magnet 22, an implant spring 24, and a bio-compatible implant body 26 having suture wings 28. Occluding magnet 22, which is rigidly affixed to one end of implant spring 24, is preferably fabricated from neodymium, samarium-cobalt, alnico, ferrite, and other magnet compositions that provide a combination of low weight and substantial magnetic flux density. Implant spring 24 comprises a longitudinally split tube of generally "C" shaped cross-section, and is preferably fabricated from bio-compatible materials, for exemplary and non-limiting purpose such as stainless steel, titanium, Ultra-High Molecular Weight (UHMW) polyethylene, and other similar or alternative resilient, strong, and fracture-resistant materials.

To both better isolate occluding magnet 22 and implant spring 24, and to provide an improved surgical implantation assembly, implant body 26 encompasses occluding magnet 22 and implant spring 24. Implant body 26 is preferably fabricated from bio-compatible materials, for exemplary and non-limiting purpose such as silicone rubber and other similar or alternative elastomeric materials, but inclusive of thermoplastic and other bio-compatible materials. In some alternative embodiment where additional strength is desired or for other benefit, implant body 26 may further comprise a bio-compatible reinforcing material such as a polyester mesh in combination with a bio-compatible material such as silicone rubber. While implant body 26 in the region adjacent to occluding magnet 22 is illustrated as being thicker in a radial direction and then thinning in the radial direction prior to widening again adjacent suture wings 28, it will be understood that those reasonably skilled in the art will determine an appropriate dimension that may deviate from that illustrated. In some embodiments, this thickening adjacent occluding magnet 22 will be exaggerated. In other embodiments there will be no thickening at all in implant body 26 in the region adjacent to occluding magnet 22.

Implant body 26 will also preferably comprise suture wings 28 that facilitate surgical coupling of surgically implanted occluding assembly 20 to surrounding body tissue, for exemplary and non-limiting purpose in males to the tunical albuginea, urethral corpus spongiosum, deep (Buck's) fascia, or other structure. As will be appreciated, the suitability of coupling to a particular body tissue preferably will be determined at design time by those reasonably skilled in the art of penile surgical implantation. Once a particular body tissue is determined, the size and appropriate placement of suture wings 28 will then be determined.

In some alternative embodiments, instead of suture wings 28 a reinforcing mesh protrudes from implant body 26. In such embodiments, the reinforcing mesh must be allowed to become integrated into the surrounding tissue before any potentially damaging forces are applied to surgically implanted occluding assembly 20. To reduce the post-surgery time required to begin using preferred embodiment male continence device 10 over the sole use of reinforcing mesh, in yet further alternative embodiments both suture wings 28 and a reinforcing mesh are provided that each protrude from implant body 26.

Surgically implanted occluding assembly 20 is configured to normally occlude urethra 3, as best illustrated in FIG. 3. To do so, implant spring 24 is shaped and dimensioned in combination with the portion of implant body 26 circumscribed by implant spring 24 to close sufficiently around urethra 3 to cause occlusion when implant spring 24 is in a substantially unbiased and substantially relaxed state. The direction of travel 36 of occluding magnet 22 just prior to the steady state position illustrated in FIG. 3, which is controlled by the natural and unbiased "C" shape of implant spring 24, is toward and very gently pressing against urethra 3. While there will be a slight force generated by urethra 3 in a direction opposite to the direction of travel arrow 36, to avoid tissue damage and necrosis this force is understood to be very small, sufficient only to prevent bladder leakage from passing through.

To selectively open urethra 3, as best illustrated in FIGS. 2 and 4, external selective occlusion control assembly 30 is brought into proximity with surgically implanted occluding assembly 20. A magnetic force is applied to occluding magnet 22 by bringing external selective control magnet 32 adjacent thereto. This magnetic force will hold external selective occlusion control assembly 30 adjacent to penis 1 and surgically implanted occluding assembly 20. In addition, the spring force generated by implant spring 24 is opposed and overcome sufficiently by this same magnetic force to open implant spring 24 and urethra 3. Notably, and similar to the spring force generated by implant spring 24, this magnetic force is preferably only sufficiently great to reliably open urethra 3. Greater forces than required for reliable operation will apply undesirably excessive forces to the tissues to which suture wings 28 are anchored, and will also undesirably excessively compress the penile tissue located between external selective occlusion control assembly 30 and surgically implanted occluding assembly 20. The direction of travel 36 of occluding magnet 22 prior to the steady state illustrated in FIG. 4 is controlled by a combination of spring force generated by implant spring 24 and magnetic force applied to occluding magnet 22 by external selective control magnet 32.

Because movement of occluding magnet 22 is constrained and controlled by implant spring 24, there is less torsional stress on the surrounding tissue even in the event of misalignment between external selective control magnet 32 and occluding magnet 22. Further, forces generated by external selective occlusion control assembly 30 will most preferably be distributed by surgically implanted occluding assembly 20. Consequently, design of the geometry of implant spring 24 will preferably take into consideration both this desired reduction of torsional stress and distribution of forces generated by bringing external selective occlusion control assembly 30 adjacent to surgically implanted occluding assembly 20.

To provide a more comfortable and readily handled external assembly, a non-allergenic or bio-compatible body 34 preferably at least partially encompasses and contains external selective control magnet 32. Body 34 may be provided with any suitable coatings, textures, surface finishes and the like as may be deemed desirable to improve the comfort, handling, and performance of external selective occlusion control assembly 30.

Various embodiments of apparatus designed in accord with the present invention have been illustrated in the various figures. The embodiments are distinguished by the hundreds digit, and various components within each embodiment designated by the ones and tens digits. However, many of the components are alike or similar between embodiments, so numbering of the ones and tens digits have been maintained wherever possible, such that identical, like or similar functions may more readily be identified between the embodiments. If not otherwise expressed, those skilled in the art will readily recognize the similarities and understand that in many cases like numbered ones and tens digit components may be substituted from one embodiment to another in accord with the present teachings, except where such substitution would otherwise destroy operation of the embodiment. Consequently, those skilled in the art will readily determine the function and operation of many of the components illustrated herein without unnecessary additional description.

A first alternative embodiment male continence device 110 is illustrated in FIGS. 6-8. In this embodiment, external selective occlusion control assembly 130 comprises a body 134 in the geometry of a circumscribing band that is wrapped about penis 1. To facilitate securement and removal, a strap 135 securely and preferably permanently anchored on a first end 137 to body 134, and is removably affixed on a second end 138 to body 134. Second end 138 may be affixed with any of the myriad of suitable fasteners known in the mechanical arts, for exemplary and non-limiting purpose only including velcro, magnetic fasteners, pressure sensitive adhesive, buttons, and clips. As may be appreciated, body 134 including strap 135 is an alternative embodiment to body 34, and may be used as the sole difference in some alternative embodiments.

However, in first alternative embodiment male continence device 110 this is not the only difference. As illustrated in FIG. 8, urethra 3 is un-occluded when surgically implanted occluding assembly 120 is free from exposure to external selective occlusion control assembly 130. The direction of travel 136 of occluding magnet 122 prior to the steady state illustrated in FIG. 8 is controlled by spring force generated by implant spring 124 returning implant spring 124 to an open and non-occluding position.

As illustrated in FIG. 7, the urethra is occluded in first alternative embodiment male continence device 110 when body 134 is wrapped about penis 1 and external selective control magnet 132 is brought adjacent to occluding magnet 122. The degree of occlusion is controlled by the magnetic flux density of each of occluding magnet 122 and external selective control magnet 132, and the spacing between these magnets. In this position illustrated in FIG. 7, the direction of travel 136 of occluding magnet 122 prior to the steady state illustrated in FIG. 7 is controlled by a combination of spring force generated by implant spring 124 and magnetic force applied to occluding magnet 122 by external selective control magnet 132. Since the magnetic force applied to occluding magnet 122 by external selective control magnet 132 tends to push external selective control magnet 132 away from penis 1, some type of apparatus such as the illustrated body 134 must be provided to hold external selective occlusion control assembly 130 adjacent to penis 1.

This operation of first alternative embodiment male continence device 110 is reversed from that of preferred embodiment male continence device 10. For the purposes of the present disclosure, preferred embodiment male continence device 10 is referred to as normally closed, and only opened when external selective occlusion control assembly 30 is applied. In contrast, first alternative embodiment male continence device 110 is referred to herein as normally open, and only closed when external selective occlusion control assembly 130 is applied.

While not illustrated in the others of FIGS. 1-8, FIG. 5 illustrates the inclusion of an optional magnetically susceptible or magnetic material 25, the teachings which may be incorporated into either surgically implanted occluding assembly 20 or surgically implanted occluding assembly 120. The optional magnetically susceptible or magnetic material 25 is configured to interact with the magnetic field produced by occluding magnet 22 to provide a magnetically induced biasing force intended to further complement or even replace the spring function of implant spring 24. For exemplary and non-limiting purpose, and as illustrated in FIG. 3, implant spring 24 within surgically implanted occluding assembly 20 is configured to occlude urethra 3 when no external magnetic field is applied. Consequently, where an optional paramagnetic material 25 is provided, the resulting magnetic force attracting occluding magnet 22 and paramagnetic material 25 together augments or in some alternative embodiments completely replaces any spring force within implant spring 24. Likewise, a magnet 25 with a pole opposite in polarity to and facing occluding magnet 22 will similarly generate a magnetic force of attraction.

In contrast, if an optional diamagnetic material 125 is provided to surgically implanted occluding assembly 120, the resulting magnetic force repelling occluding magnet 122 from diamagnetic material 125 augments or in some alternative embodiments completely replaces any spring force within implant spring 124. Likewise, a magnet 125, that is also not illustrated but similar to and placed like material 25 in FIG. 5, with a pole of like polarity to and facing occluding magnet 122 will similarly generate a magnetic force of repulsion.

The inclusion of an optional magnetically susceptible or magnetic material 25, 125 enables a designer to split either surgically implanted occluding assembly 20 or surgically implanted occluding assembly 120 into two pieces, each that will then be surgically implanted separately one from the other. In such case, rather than trying to couple separate portions of implant spring 24, 124 together to couple the spring force fully through the final "C"-shaped cross-section, this force magnetically induced by optional magnetically susceptible or magnetic material 25, 125 can, as noted herein above, be used to eliminate the need for implant spring 24, 124 to generate any spring force.

As illustrated in FIGS. 9-11, a second alternative embodiment surgically implanted occluding assembly 220 comprises a generally "C"-shaped cross-section bio-compatible implant body 226. As illustrated, implant body 226 does not have suture wings. Nevertheless, suture wings similar to those described herein above with reference to suture wings 28 that are configured to facilitate surgical coupling of surgically implanted occluding assembly 220 to surrounding body tissue may optionally be provided.

As with implant body 26, implant body 226 is preferably fabricated from bio-compatible materials, for exemplary and non-limiting purpose such as silicone rubber and other similar or alternative elastomeric materials. However, implant body 226 is either inherently quite resilient and rigid, or is further provided with an internal stiffener that is preferably fabricated from bio-compatible materials, for exemplary and non-limiting purpose such as stainless steel, titanium, Ultra-High Molecular Weight (UHMW) polyethylene, and other similar or alternative resilient, strong, and fracture-resistant materials.

Bridging the gap between the ends of the generally "C"-shaped cross-section in implant body 226 is a bi-stable spring 221 that is slightly longer than the gap. By being slightly longer than the gap, bi-stable spring 221 will be forced to form a gentle arc, either inward toward urethra 3 and therefore into a position occluding the urethra as illustrated in FIG. 10, or outward away from urethra 3 and therefore into a position opening the urethra as illustrated in FIG. 11.

While the generally "C"-shaped cross-section in implant body 226 is stiffer than bi-stable spring 221, it will most preferably flex sufficiently during the transitional movement of bi-stable spring 221 between the two stable positions of FIGS. 10 and 11 to permit the momentary straightening of bi-stable spring 221 during such transitional movement.

Switching bi-stable spring 221 from the un-occluding position illustrated in FIG. 11 to the occluding position illustrated in FIG. 10 only requires a minor amount of pressure to be manually applied to the exterior of penis 1 near the center of bi-stable spring 221 and in an inward direction toward the geometric center of occluding assembly 220. This will cause bi-stable spring 221 to initially straighten, in turn generating a slight expansion in the gap between the ends of the generally "C"-shaped cross-section of implant body 226. This slight expansion in the gap between the ends of the generally "C"-shaped cross-section of implant body 226 creates a storing of potential energy within implant body 226 while bi-stable spring 221 initially straightens. When bi-stable spring 221 moves beyond the straight position and starts to curve inward, the potential energy stored within implant body 226 is quickly released, resulting in a tactile snap confirming the change of state of bi-stable spring 221 to the occluding position.

In contrast, switching bi-stable spring 221 in the other direction, from the occluding position illustrated in FIG. 10 to the un-occluding position illustrated in FIG. 11 requires a force to pull bi-stable spring 221 outward. This is achieved in second alternative embodiment male continence device 210 through the provision of occluding magnet 222 that is rigidly coupled to bi-stable spring 221. An external magnet of any suitable geometry, for exemplary and non-limiting purpose including the geometries of external selective occlusion control assembly 30 and 130 described herein above as well as a bare magnet or other suitably covered or encapsulated magnet, will be used in various embodiments to implement the external selective occlusion control assembly 230 portion of second alternative embodiment male continence device 210.

In the event of an unlikely failure that somehow prevents an external selective occlusion control assembly or external selective occlusion control magnet from activating bi-stable spring 221 to an open or un-occluded position, a standard balloon catheter can be inserted and inflated by medical personnel to open urethra 3. If bi-stable spring 221 remains functional, once opened by the balloon catheter a patient can then schedule a urology visit at their and their doctor's convenience during normal office hours.

While not separately illustrated, in some embodiments a coating, further encapsulation, or even extension of implant body 226 may fully circumscribe urethra 3, including bi-stable spring 221 and occluding magnet 222. In such embodiments, a stiffer internal member will necessarily be provided internally to the illustrated implant body 226. Said another way, if the illustrated implant body 226 is a relatively stiffer spring member, a relatively softer coating, for exemplary and non-limiting purpose such as a low-durometer silicone rubber elastomer, may encapsulate the entirety of implant body 226, bi-stable spring 221, and occluding magnet 222 to thereby fully circumscribe urethra 3.

Figure 13:
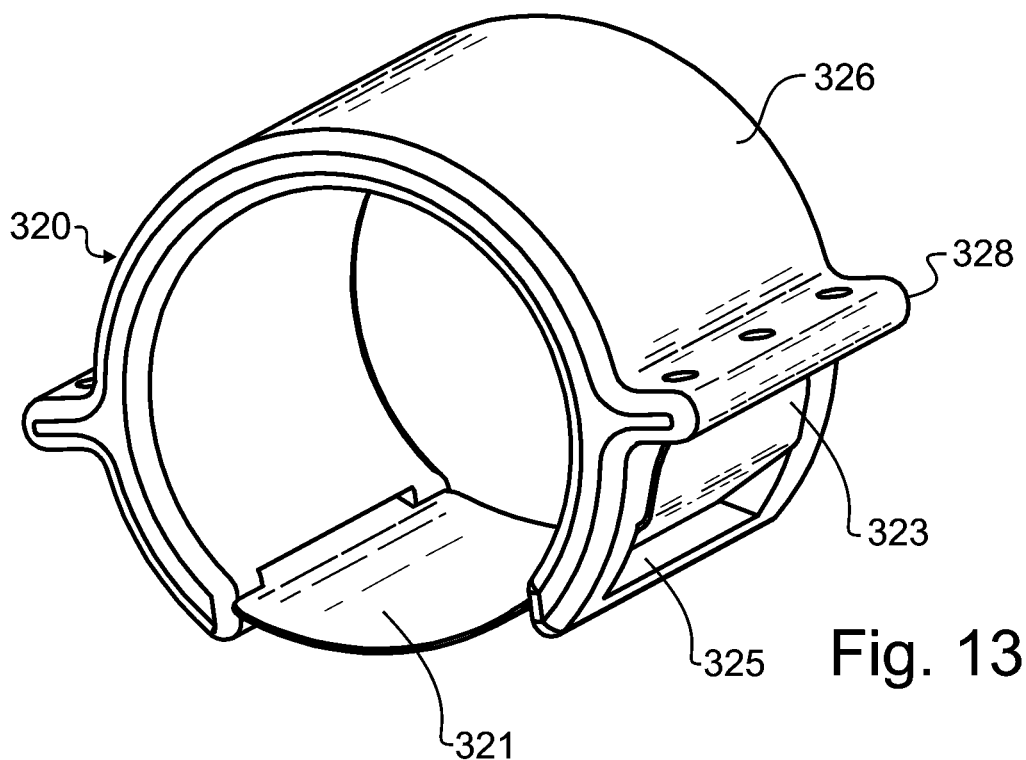
FIG. 13 illustrates the second alternative embodiment occluding assembly of FIG. 12 from a projected view, without an occluding magnet and with suture wings, and showing the urethra un-occluded.
Figure 14:
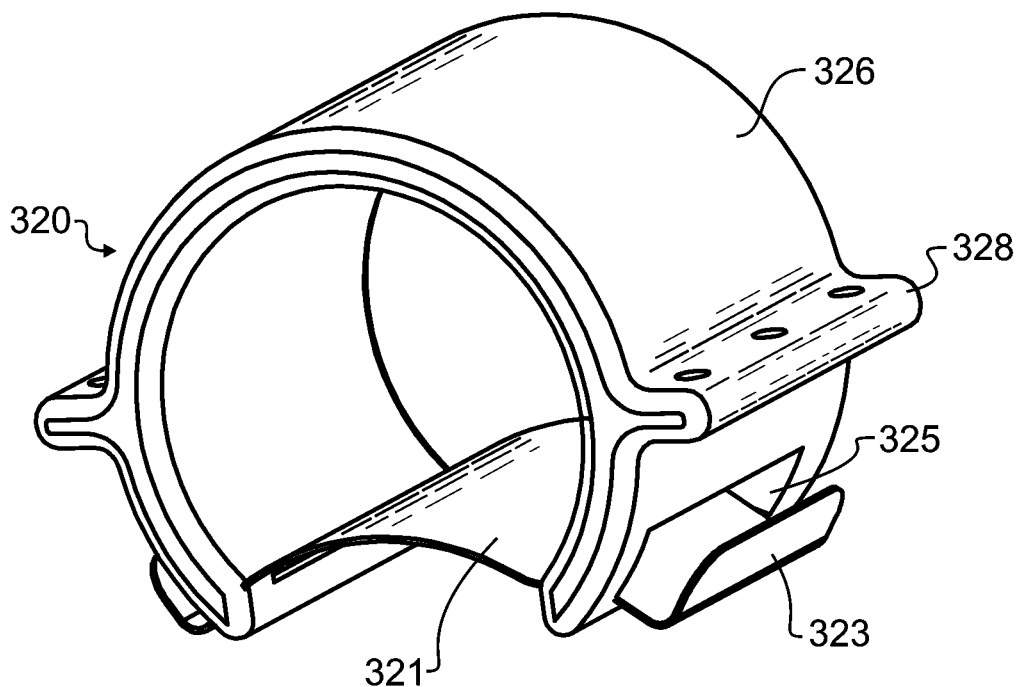
FIG. 14 illustrates the second alternative embodiment surgically implanted occluding assembly of FIG. 13 from a projected view, showing the urethra occluded.

FIG. 12 illustrates a third alternative embodiment occluding assembly 320 prior to surgical implanting and with an occluding magnet 322 and suture wings 328. FIGS. 13 and 14 illustrate the third alternative embodiment occluding assembly 320, but without an occluding magnet 322 and in un-occluded and occluded positions, respectively.

Similar to bi-stable spring 221, bi-stable spring 321 bridges the gap between the ends of the generally "C"-shaped cross-section in implant body 326, and is slightly longer than the gap. By being slightly longer than the gap, bi-stable spring 321 will be forced to form a gentle arc, either inward toward urethra 3 and therefore into a position occluding the urethra as illustrated in FIG. 14, or outward away from urethra 3 and therefore into a position opening the urethra as illustrated in FIGS. 12 and 13.

While the generally "C"-shaped cross-section in implant body 326 is stiffer than bi-stable spring 321, and in some embodiments will be rigid, in some other embodiments it will flex sufficiently during the transitional movement of bi-stable spring 321 between the two stable positions of FIGS. 13 and 14 to facilitate the momentary straightening of bi-stable spring 321 during such transitional movement.

However, differing from second alternative embodiment occluding assembly 220, the third alternative embodiment occluding assembly 320 includes a pair of opposed openings 325. Each of these openings passes through bio-compatible implant body 326 adjacent to the gap in the generally "C"-shaped cross-section. Further differing, while bi-stable spring 321 has a relatively wider body that cannot pass through openings 325, it is also provided with bi-stable spring ends 323 that do pass through. The presence of this pair of bi-stable spring ends 323, each passing through an adjacent one of the opposed openings 325, allows bi-stable spring 321 to pass through while not being affixed to implant body 326. In effect, bi-stable spring 321 uses the openings 325 and the immediately adjacent portions of implant body 326 as pivot points about which bi-stable spring 321 pivots when snapping between occluding and non-occluding positions. This simplified pivotal coupling between bi-stable spring 321 and implant body 326 permits a wider selection of materials and associated stiffness for both implant body 326 and bi-stable spring 321.

In addition, bi-stable spring ends 323 retain bi-stable spring 321 within implant body 326 and as visible in FIG. 14 also provide a point of manual contact to activate bi-stable spring 321. A person may grasp bi-stable spring ends 323 and push against the edge of openings 325 to transition or snap bi-stable spring 321 from the occluding position of FIG. 14 to the un-occluding position of FIG. 13. This extension is necessary without occluding magnet 322, as illustrated in FIG. 14, to allow a person to switch bi-stable spring 321.

In contrast, switching bi-stable spring 321 in the other direction from the un-occluding position illustrated in FIG. 13 to the occluding position illustrated in FIG. 14 only requires a minor amount of pressure to be manually applied to the exterior of penis 1 near the center of bi-stable spring 321 and in an inward direction toward the geometric center of occluding assembly 320. This will cause bi-stable spring 321 to initially straighten, in turn generating a slight expansion in the gap between the ends of the generally "C"-shaped cross-section of implant body 326. This slight expansion in the gap between the ends of the generally "C"-shaped cross-section of implant body 326 creates a storing of potential energy within implant body 326 while bi-stable spring 321 initially straightens. When bi-stable spring 321 moves beyond the straight position and starts to curve inward, the potential energy stored within implant body 326 is quickly released, resulting in some embodiments in a tactile snap confirming the change of state of bi-stable spring 321 to the occluding position.

As is thus apparent, manual techniques are provided for switching bi-stable spring 321 in either direction. Nevertheless, the optional occluding magnet 322 illustrated in FIG. 12 may be used in combination with an external selective occlusion control assembly in the same manner as occluding magnet 222, in addition to or instead of the above manual switching techniques.

In some embodiments, the ends 323 of bi-stable spring 321 are designed to stay in the vicinity of openings 325, to thereby reduce any rubbing or other potentially adverse interaction with surrounding penile tissue. Ends 323 will in some further embodiments be covered by gently stretched silicone rubber bands or sleeves, heat shrinkable bio-compatible polymers, or other suitable enclosures to at least in part encapsulate and isolate one or both ends 323 of bi-stable spring 321 from surrounding penile tissue.

Similarly, while both ends 323 are shown as being turned approximately perpendicular to the immediately adjacent main body of bi-stable spring 321, in some less desirable alternative embodiments one of the two ends 323 may comprise a full circular loop that is wrapped about a pin, rod, tube, or similar structure that extends through opening 325 in the manner of a wristwatch pin, thereby limiting the travel of that looped end 323 to primarily circular motion. The looped end is less desirable since activation of bi-stable spring 321 along the un-looped end 323 will generate undesirable torsional forces.

While the preferred and alternative embodiments of the invention are disclosed as apparatus for the express purpose of controlling urinary incontinence, in some alternative embodiments the present invention will be applied by those skilled in the art to other applications requiring a body-implanted lumen occluding apparatus.

While the foregoing details what is felt to be the preferred embodiment of the invention, no material limitations to the scope of the claimed invention are intended. Further, features and design alternatives that would be obvious to one of ordinary skill in the art are considered to be incorporated herein. The scope of the invention is set forth and particularly described in the claims herein below.

We claim:

1. An occluding assembly configured to be surgically implanted and selectively occlude an anatomical lumen, said occluding assembly comprising:

an implant body having a longitudinally split tube of generally "C"-shaped cross-section configured to circumscribe said anatomical lumen and thereby defining a longitudinally extensive gap; and a bi-stable spring having a body longer than and spanning said longitudinally extensive gap in said implant body and having a first stable anatomical lumen occluding position curved toward said anatomical lumen and thereby configured to occlude said anatomical lumen, and a second stable anatomical lumen un-occluding position curved outward away from said anatomical lumen and thereby configured to leave said anatomical lumen un-occluded;

wherein said bi-stable spring passes through a first radial opening and a second radial opening, each opening extending through said implant body adjacent to and on opposed sides of said longitudinally extensive gap; and wherein said bi-stable spring body is blocked from passing through said radial openings.

2. The occluding assembly of claim 1, wherein said bi-stable spring body is anchored in a bi-stable spring body first location to said longitudinally split tube adjacent to a first termination of said generally "C"-shaped cross-section, and is anchored in a bi-stable spring body second location distal to said bi-stable spring body first location adjacent to a second termination of said generally "C"-shaped cross-section, said second termination of said generally "C"-shaped cross-section spaced from said first termination of said generally "C"-shaped cross-section by of said longitudinally extensive gap.

3. The occluding assembly of claim 2, wherein said bi-stable spring body is further configured to press against said first and second terminations of said generally "C"-shaped cross-section and store potential energy when activated.

4. The occluding assembly of claim 1, wherein
said bi-stable spring body is wider than said first and second radial openings.

5. The occluding assembly of claim 1, wherein said bi-stable spring further comprises a first and second bi-stable spring end terminating and protruding from said bi-stable spring body at distal ends thereof, said first and second bi-stable spring ends passing through said first radial opening and said second radial opening, respectively.

6. The occluding assembly of claim 1, wherein said anatomical lumen comprises a urethra, and in said first stable anatomical lumen occluding position said urethra is occluded to prevent urinary incontinence.

7. The occluding assembly of claim 1, further comprising an occluding magnet configured to transpose said bi-stable spring from said first stable anatomical lumen occluding position to said second stable anatomical lumen un-occluding position.

8. The occluding assembly of claim 1, wherein said implant body further comprises suture wings.

* * * * *